United States Patent
Dahl et al.

(10) Patent No.: US 7,518,106 B2
(45) Date of Patent: Apr. 14, 2009

(54) ION MOBILITY SPECTROMETERS AND METHODS FOR ION MOBILITY SPECTROMETRY

(75) Inventors: David A. Dahl, Idaho Falls, ID (US); Jill R. Scott, Idaho Falls, ID (US); Anthony D. Appelhans, Idaho Falls, ID (US); Timothy R. McJunkin, Idaho Falls, ID (US); John E. Olson, Rigby, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 377 days.

(21) Appl. No.: 11/610,633

(22) Filed: Dec. 14, 2006

(65) Prior Publication Data

US 2008/0142700 A1  Jun. 19, 2008

(51) Int. Cl.
*H01J 49/40* (2006.01)
*H01J 49/00* (2006.01)

(52) U.S. Cl. .................... 250/286; 250/281; 250/282; 250/299

(58) Field of Classification Search ......... 250/281–283, 250/286–290, 293, 299
See application file for complete search history.

(56) References Cited

U.S. PATENT DOCUMENTS

| | | | | |
|---|---|---|---|---|
| 3,153,742 A | * | 10/1964 | Kluver | ..................... 315/3 |
| 5,189,301 A | * | 2/1993 | Thekkadath | ............... 250/287 |
| 5,796,100 A | | 8/1998 | Palermo | |
| 6,100,521 A | | 8/2000 | Doring et al. | |
| 6,627,883 B2 | | 9/2003 | Wang et al. | |
| 6,646,258 B2 | | 11/2003 | Russ, IV | |
| 6,649,911 B2 | | 11/2003 | Kawato | |
| 6,670,606 B2 | | 12/2003 | Verentchikov et al. | |
| 6,674,067 B2 | | 1/2004 | Grosshans et al. | |
| 6,674,071 B2 | | 1/2004 | Franzen et al. | |
| 6,690,005 B2 | | 2/2004 | Jenkins et al. | |
| 6,700,116 B2 | | 3/2004 | Taniguchi | |
| 6,713,757 B2 | | 3/2004 | Tanner et al. | |
| 6,888,128 B2 | | 5/2005 | Krasnobaev et al. | |
| 7,038,216 B1 | * | 5/2006 | Dahl et al. | ............ 250/423 R |
| 7,259,369 B2 | * | 8/2007 | Scott et al. | ............... 250/287 |
| 2008/0142697 A1 | * | 6/2008 | Dahl et al. | ................ 250/282 |
| 2008/0142700 A1 | * | 6/2008 | Dahl et al. | ................ 250/286 |

* cited by examiner

*Primary Examiner*—Bernard E Souw
(74) *Attorney, Agent, or Firm*—Fennemore Craig, PC

(57) ABSTRACT

An ion mobility spectrometer may include an inner electrode and an outer electrode arranged so that at least a portion of the outer electrode surrounds at least a portion of the inner electrode and defines a drift space therebetween. The inner and outer electrodes are electrically insulated from one another so that a non-linear electric field is created in the drift space when an electric potential is placed on the inner and outer electrodes. An ion source operatively associated with the ion mobility spectrometer releases ions to the drift space defined between the inner and outer electrodes. A detector operatively associated with at least a portion of the outer electrode detects ions from the drift space.

23 Claims, 10 Drawing Sheets

ION MOBILITY SPECTROMETERS AND METHODS FOR ION MOBILITY SPECTROMETRY

GOVERNMENT RIGHTS

This invention was made with United States Government support under Contract No. DE-AC07-05ID14517 awarded by the United States Department of Energy. The United States Government has certain rights in the invention.

TECHNICAL FIELD

This invention relates to ion mobility spectrometry in general and more specifically to ion mobility spectrometry methods and ion mobility spectrometers having improved sensitivities and resolutions.

BACKGROUND OF THE INVENTION

Ion mobility spectrometry is a technique that separates and detects electrically charged particles (e.g., ions) that have been sorted according to how fast they travel through an electrical field in a chamber containing a gas, typically at atmospheric pressure. Small ions travel through the gas faster than do large ions (due to viscous effects) and reach the end of the chamber first, with successively larger ions arriving later. Because ion mobility spectrometry only sorts ions by size (i.e., cross-sectional area per unit charge), and not by their chemical properties or other identifying features, it cannot be used in all cases to make a positive identification of unknown compounds. However, ion mobility spectrometers can be used with certain compounds and can make measurements quite rapidly (e.g., in only a few seconds), therefore making them highly desirable for use in certain applications (e.g., warning and/or screening devices). For example, ion mobility spectrometers are commonly used to detect explosives, narcotics, and chemical warfare (e.g., nerve and blister) agents.

A typical ion mobility spectrometer comprises an ionization region, a drift chamber, and a detector. The ionization region is located at one end of the drift chamber, while the detector is located at the other end of the drift chamber. The ionization region is typically provided with a radioactive source, such as $^{63}$Ni, suitable for ionizing the sample material, although other ionizing techniques may be used. Ions of the sample material from the ionization region are introduced into the drift chamber (e.g., either by a fixed open time shutter or by a fixed width gating design), whereupon they ultimately reach the detector at the far end. The arriving ions cause the detector to generate electrical signal peaks proportional to the rate of arriving ions which may thereafter be interpreted to form a conclusion about the nature of the sample material.

While ion mobility spectrometers of the type just described work well and are being used, they are not without their disadvantages. For example, ion diffusion and ion charge-repulsion effects tend to diminish the sensitivity and resolution of an ion mobility spectrometer. Therefore, a need remains for an ion mobility spectrometer and ion mobility spectrometry method that achieve higher resolutions and/or sensitivities when compared with currently available designs.

SUMMARY OF THE INVENTION

An ion mobility spectrometer according to the teachings provided herein may include an inner electrode and an outer electrode arranged so that at least a portion of the outer electrode surrounds at least a portion of the inner electrode and defines a drift space therebetween. The inner and outer electrodes are electrically insulated from one another so that a non-linear voltage gradient inversely proportional to radius is created between the inner and outer electrodes. This results in the field voltage varying logarithmically with the radius. An ion source operatively associated with the ion mobility spectrometer releases ions to the drift space defined between the inner and outer electrodes. A detector operatively associated with at least a portion of the outer electrode detects ions arriving from the drift space.

Also disclosed is a method for performing ion mobility spectrometry that includes: Releasing ions in a logarithmic electric field; allowing the ions to drift within the logarithmic electric field; and detecting the ions at a detector.

BRIEF DESCRIPTION OF THE DRAWING

Illustrative and presently preferred embodiment of the invention are shown in the accompanying drawing in which.

DETAILED DESCRIPTION OF THE PREFERRED EMBODIMENTS

Figure 1:
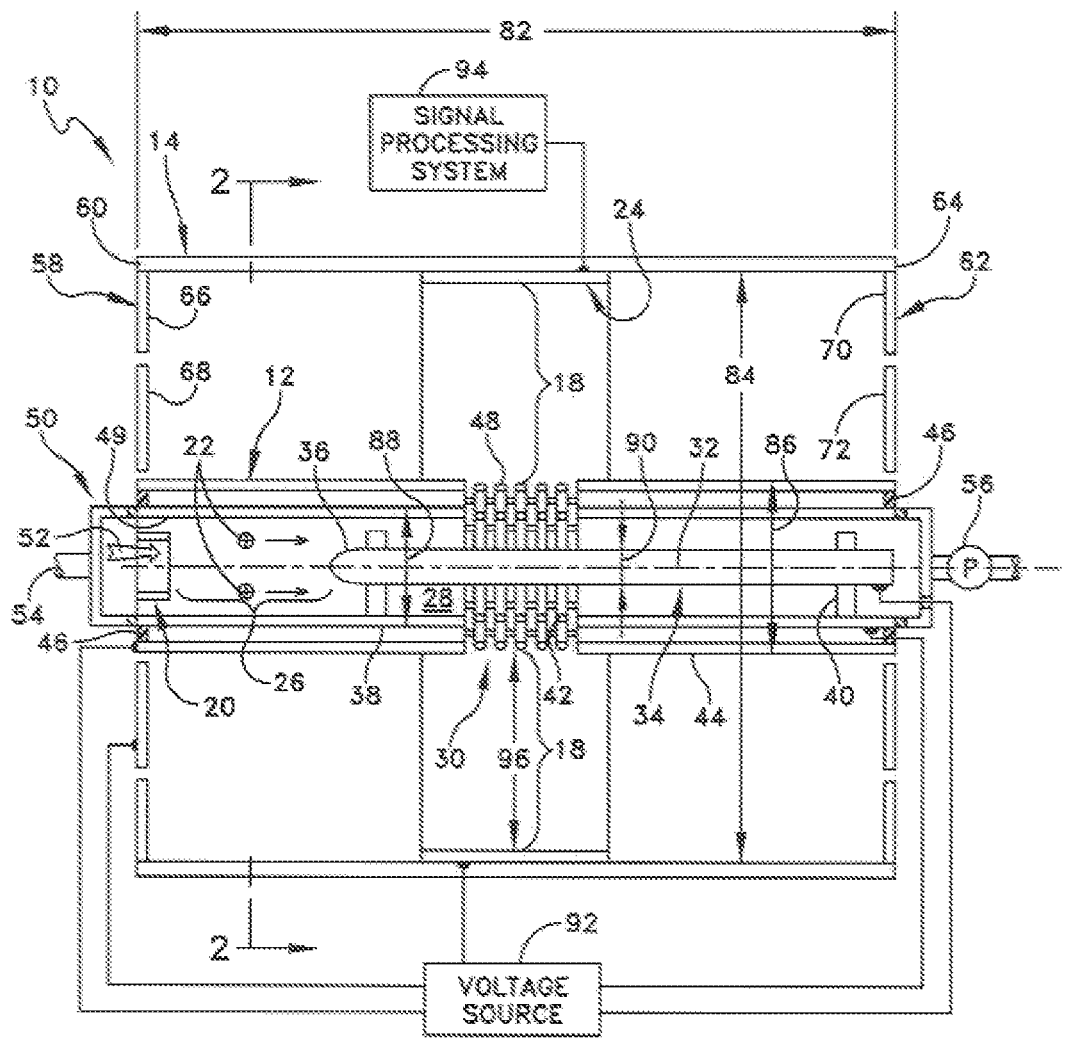
FIG. 1 is a cross-sectional side view in elevation of an ion mobility spectrometer according to one embodiment of the invention.
Figures 2, 2A:
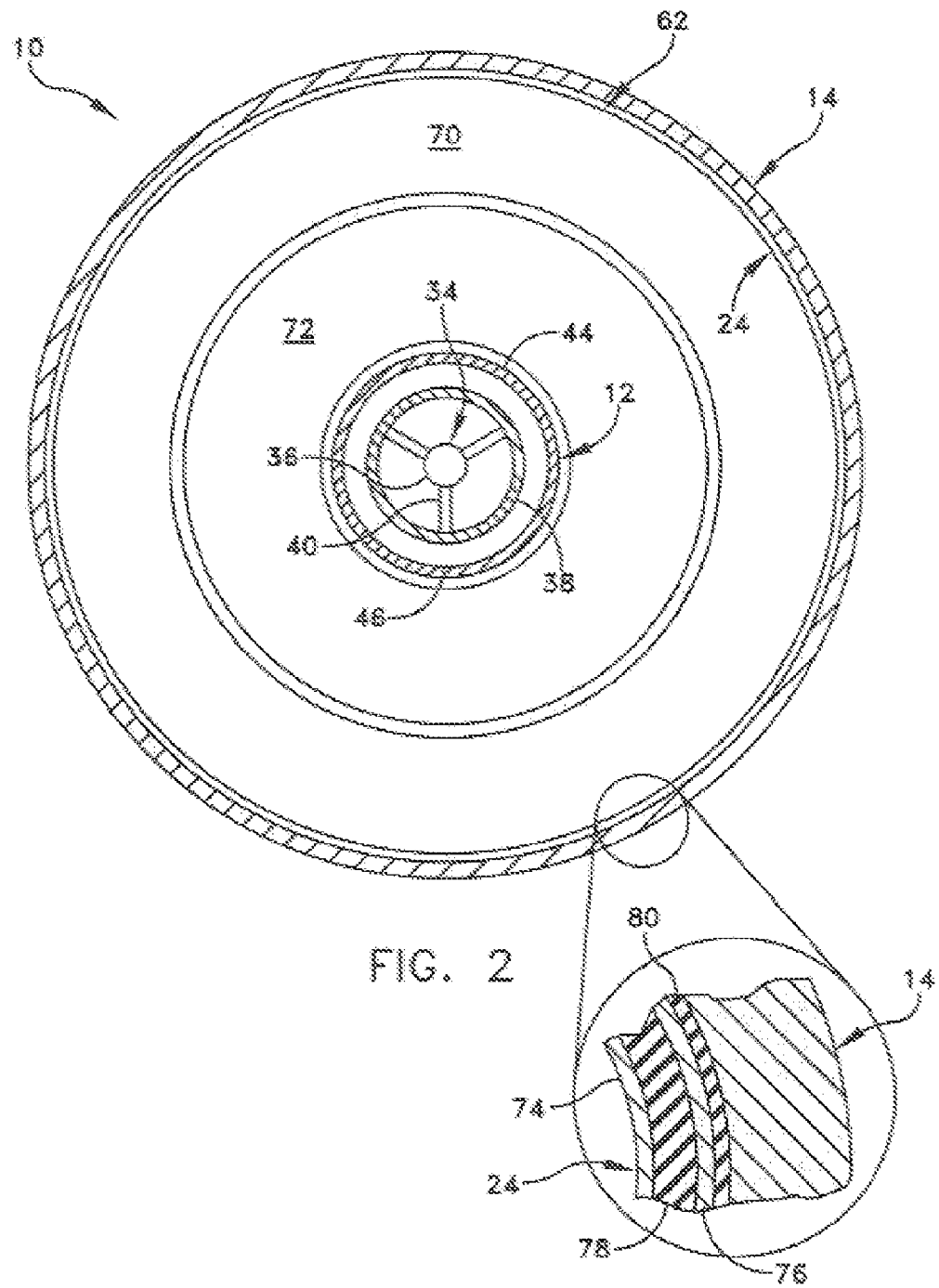
FIG. 2 is a cross-sectional end view in elevation taken along the line 2-2 of the ion mobility spectrometer illustrated in FIG. 1.
FIG. 2a is an enlarged cross-sectional view in elevation of a section of the outer electrode and detector.

Briefly described, an ion mobility spectrometer (IMS) 10 according to one embodiment of the present invention is best seen in FIGS. 1 and 2 and may comprise an inner electrode 12 and an outer electrode 14. The arrangement of the inner and outer electrodes 12 and 14 is such that at least a portion, and generally substantially the entirety, of the inner electrode 12 is surrounded by at least a portion, and generally substantially the entirety, of the outer electrode 14, provided the geometry maintains a logarithmic electrostatic field 16 in the manner described herein. The inner and outer electrodes 12 and 14 are electrically insulated from one another so that when an electric potential difference is applied between the inner and outer electrodes 12 and 14, a logarithmic (i.e., non-linear) electric field 16 (FIGS. 3 and 4) is created at least within a drift space or region 18 defined between the inner and outer electrodes 12 and 14. Ion mobility spectrometer 10 may also be provided with an ion source 20 for producing and/or ionizing a sample material (not shown) to be analyzed by ion mobility spectrometer 10. Thereafter, ions 22 of the sample material are released into the drift space 18. A detector 24 operatively associated with at least a portion of the outer electrode 14 detects ions 22 from drift space 18.

Ion mobility spectrometer 10 may be operated as follows to detect ions 22. In one embodiment, ions 22 are formed within an ion formation region 26 within an ion tunnel 28 defined by portions of the inner electrode 12, although other arrangements are possible, as will be described in further detail below. Inner electrode 12 may be provided with an ion gate or ion shutter 30 to allow ions 22 to be selectively blocked or released into the drift space 18. As will be described in greater detail below, the release process involves raising the potential of the ejection electrode 34 to create a logarithmic electric field that matches the logarithmic electric field 16 in the drift region 18, and then "opening" the ion shutter 30 by matching its potential to the logarithmic electric field. After entering the drift space 18 (e.g., via the ion shutter 30), the ions 22 will continue through the logarithmic (i.e., non-linear) electric field 16 existing in at least the drift space 18 and between the inner and outer electrodes 12 and 14. More specifically, in one embodiment wherein the inner and outer electrodes 12 and 14 comprise generally cylindrically shaped members, the non-linear electric field 16 will comprise a logarithmic field. That is, the electric potential of the field 16 decreases as a function of the square of the distance (i.e., radius) from the inner electrode 12. Alternatively, other types of non-linear electrostatic fields are possible with appropriate changes to geometry and should be regarded as within the scope of the present invention.

Figure 3:
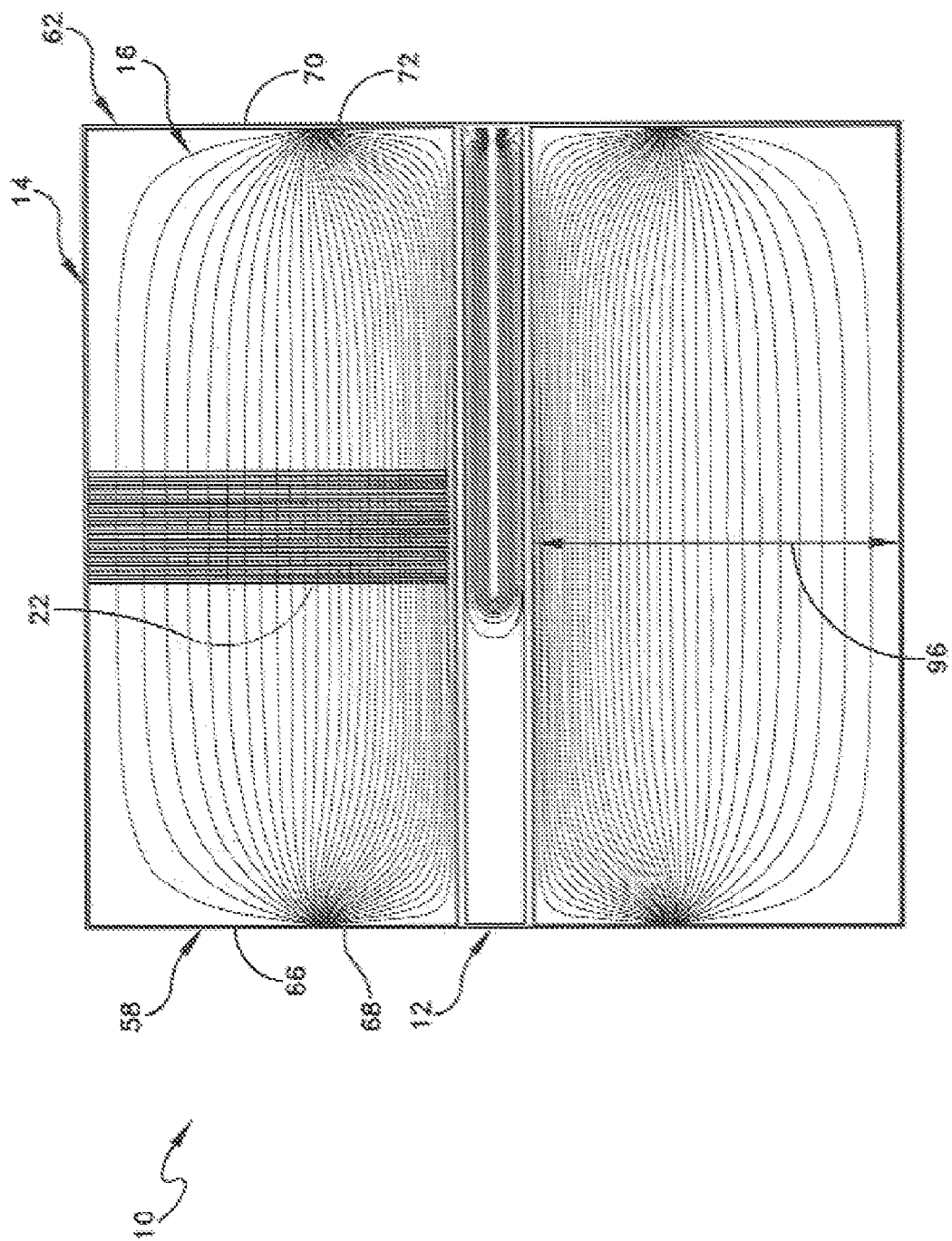
FIG. 3 is a side view simulation of electrostatic gradients produced by the ion mobility spectrometer illustrated in FIG. 1.
Figure 4:
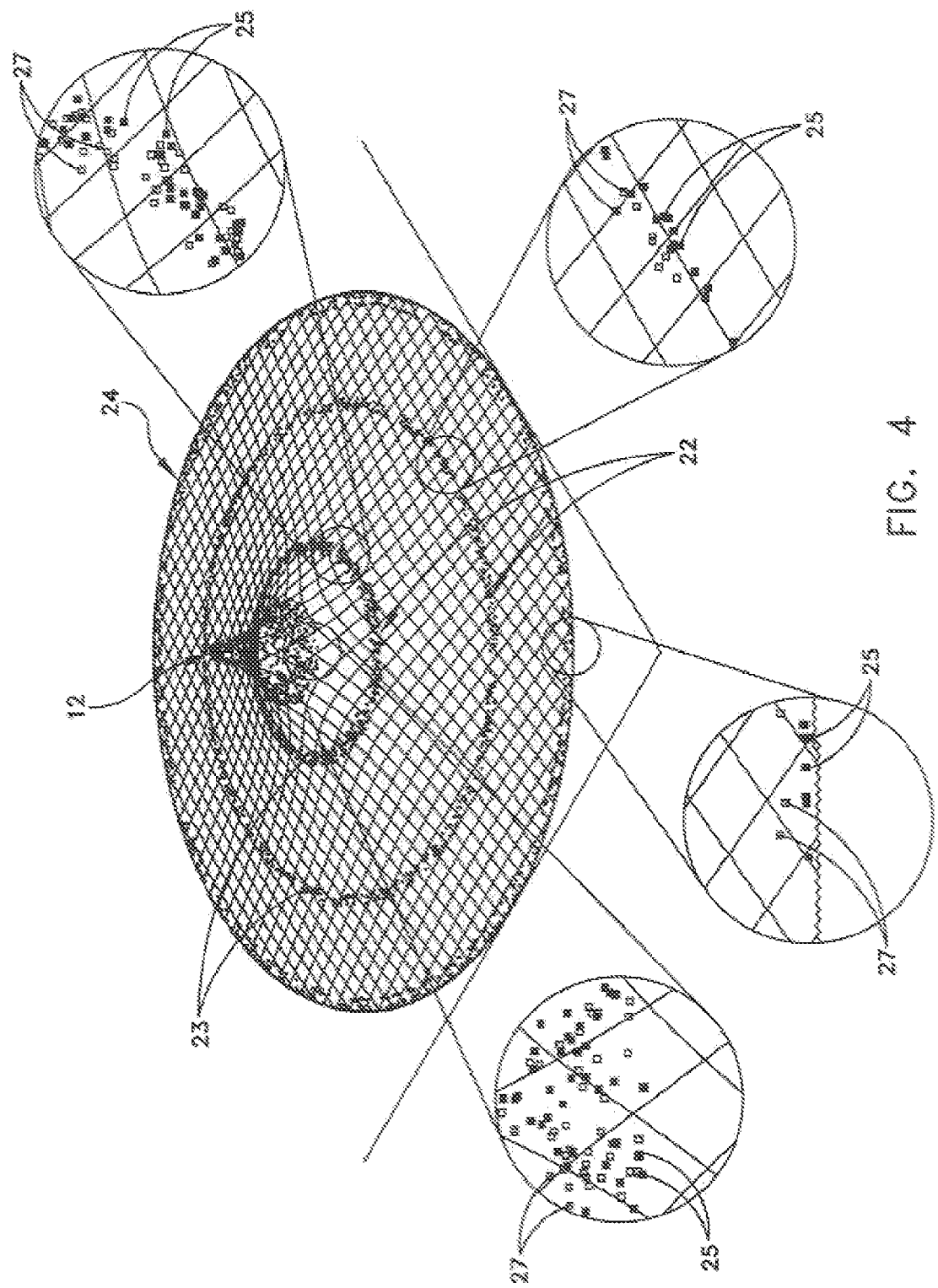
FIG. 4 is a simulation of potential energy surface view of a cylindrical, logarithmic electrostatic field of the type produced by the ion mobility spectrometer illustrated in FIG. 1 and showing possible ion trajectories.
Figure 5:
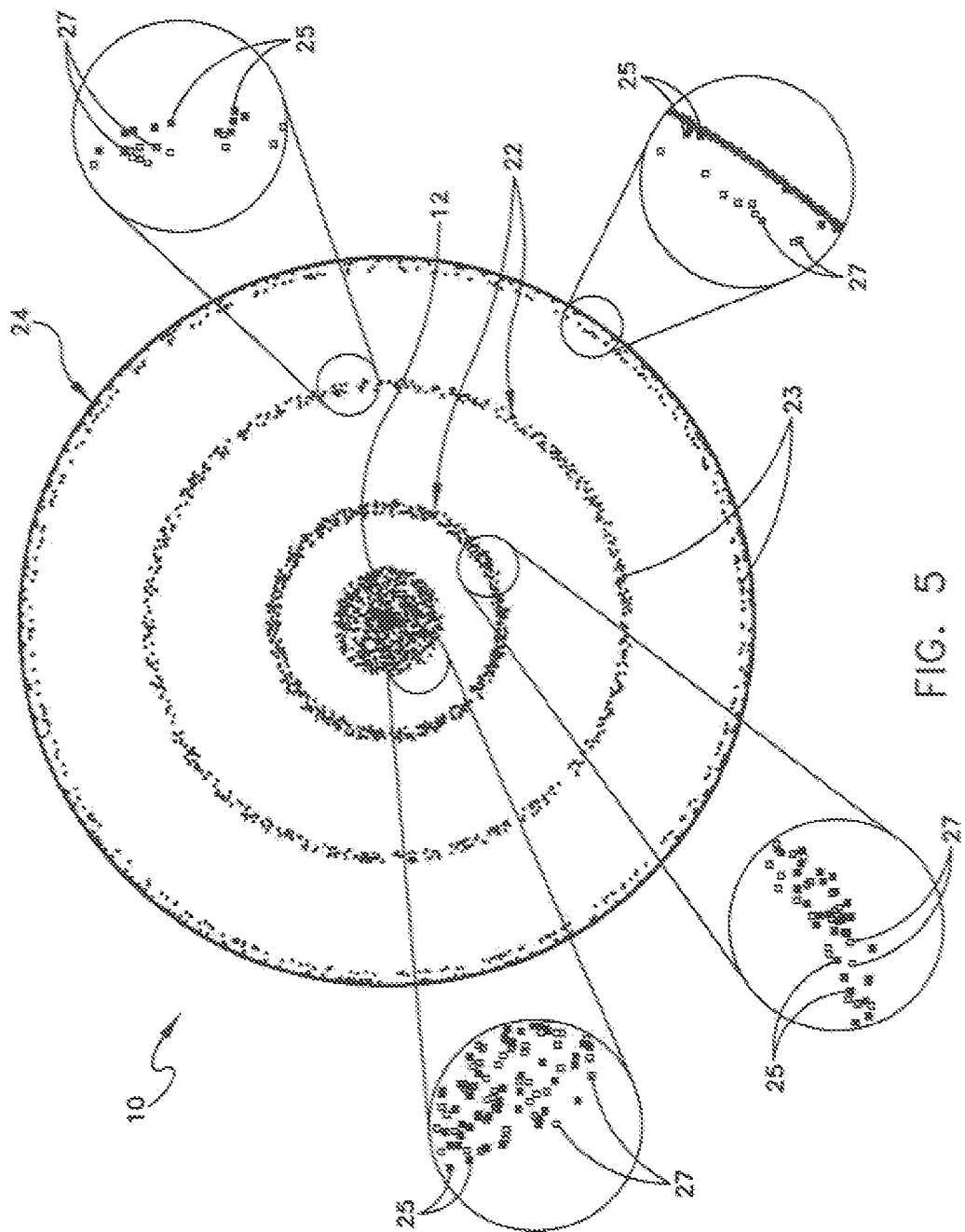
FIG. 5 is a simulation ion trajectories in a cylindrical, logarithmic electrostatic field of the type produced by the ion mobility spectrometer of FIG. 1.

Referring now primarily to FIGS. 3-5, the logarithmic electric field 16 causes the (e.g., substantially fixed width packet) ions 22, released near the center of the logarithmic electric field 16 (i.e., that extends between the ejection electrode 34 and the outer electrode 14) to migrate toward the outer electrode 14, whereupon they are detected by detector 24. As the ions 22 traverse the drift space 18, charge-repulsion and diffusion effects cause them to spread apart slightly. Significantly, however, these effects are countered to some degree by the forces imparted to the ions 22 by the logarithmic electric field 16. More specifically, in the logarithmic electric field 16 the ion velocity is inversely proportional to the radius (in viscous flow). Therefore, the leading ions 22 in the packet move more slowly than do the trailing ions in the packet. Consequently, a band 23 of identical ions 22 will tend to pack and become thinner as the band 23 moves outward. See FIG. 5. The ion density also decreases as the ions 22 in the bands 23 travel outwardly toward detector 24. The decreased ion density tends to reduce ion radial spread due to charge-repulsion effects. In summation then, the packing and thinning of the ions 22 as they traverse the drift space 18 can result in substantial increases in theoretical resolution i.e., the fractional resolving limit (discussed below), compared with currently available ion mobility spectrometers having linear electrostatic fields.

As used herein, the fractional resolving limit is defined as the percentage difference in ion mobilities that can just be resolved in theory when diffusion effects are ignored for a given ion mobility spectrometer. As will be described in further detail herein, the fractional resolving limit of an ion mobility spectrometer according to the present invention is a function of the square of the radius of the ion mobility spectrometer 10, whereas the fractional resolving limit of a conventional drift-tube IMS having a linear electrostatic field is a linear function of the drift length. Therefore, if two groups of ions 22 that vary in mobility by 1% have initial packet widths of about 1 cm, then in an ideal case, a linear IMS would require a drift length of about 100 cm to just separate or resolve the two ion packets, whereas the radius of the IMS 10 of the present invention would only need to be about 10 cm for the same initial ion packet width. In reality, of course, both IMS systems would have to be slightly larger due to several factors (e.g., diffusion effects). Therefore, the squared relation of the fractional resolving limit of an ion mobility spectrometer according to the teachings provided herein will allow for thicker initial ion packets (for the same resolution) compared to a conventional IMS having a linear electrostatic field in the drift region. Alternatively, the resolution will be increased for ion packets of the same initial thickness.

Another advantage of ion mobility spectrometers according to the present invention is that the boundary-less expansion of the ion bands 23 means that ions 22 are not lost to the walls of the drift chamber as they traverse the drift space 18. That is, a substantial portion of the ions 22 released by the ion shutter 30 will reach detector 24. In addition, diffusion effects can be reduced by either increasing the potential voltage drop across the inner and outer electrodes 12 and 14 and/or by proportionally reducing the size of the IMS 10 while retaining the same potential drop. In summation, the ion mobility spectrometer 10 according to the present invention represents a significant departure from prior art ion mobility spectrometers. Indeed, the combination of the logarithmic electric field and the boundary-less expansion of the ion bands represents a new paradigm in the field of ion mobility spectrometry.

Having briefly described one embodiment of the ion mobility spectrometer 10 according to the present invention, as well as some of its more significant features and advantages, various exemplary embodiments of the ion mobility spectrometer and methods for conducting ion mobility spectrometry will now be described in detail.

Referring back now to FIG. 1, one embodiment 10 of an ion mobility spectrometer according to the teachings of the present invention may comprise an inner electrode 12 and an outer electrode 14. In the embodiments shown and described herein, the inner and outer electrodes 12 and 14 comprise generally hollow, cylindrically-shaped structures that are concentrically positioned or "nested" with respect to one another so that they are substantially aligned along a longitudinal axis 32. That is, inner electrode 12 is substantially surrounded by the outer electrode 14.

The inner electrode 12 may comprise any of a wide variety of configurations and structural arrangements depending on the particular methodology used to produce the ions 22. For example, in one embodiment, inner electrode 12 may comprise several different elements that allow for the production of ions, the conduction of ions to a release point (i.e., adjacent the drift space 18), as well as an ion shutter 30 to allow for the periodic release of ions into the drift space.

Figure 9:
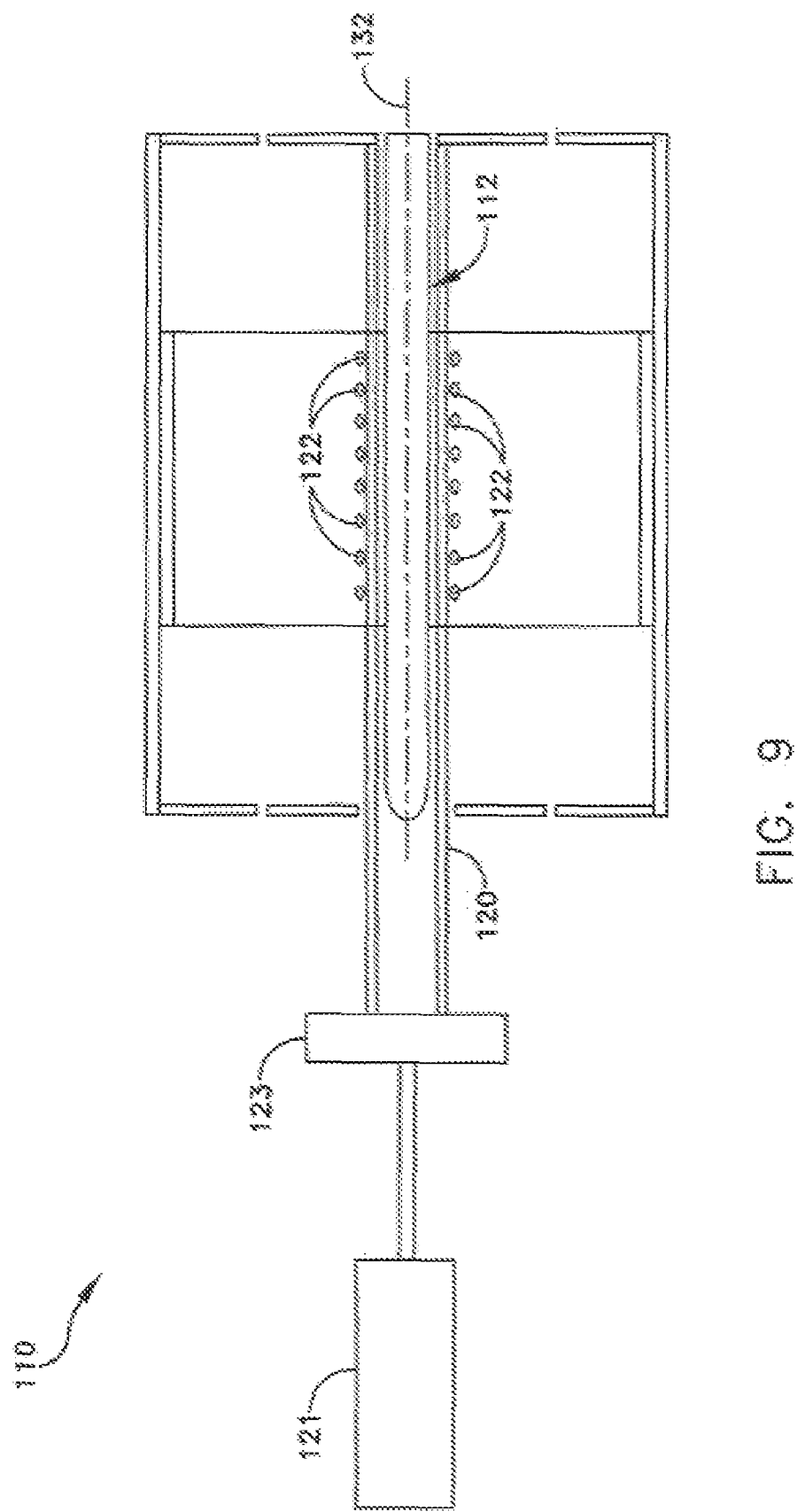
FIG. 9 is a cross-sectional side view in elevation of an ion mobility spectrometer having a laser ion source.

In an alternative embodiment, illustrated in FIG. 9, an ion mobility spectrometer 110 may comprise an inner electrode 112 having a comparatively simple, rod-like element that is generally aligned along longitudinal axis 132 of ion mobility spectrometer 110. Ions 122 may be generated in a region adjacent (i.e., around) the inner electrode 112 by a laser beam 120 produced by a laser 121. If desired, an optics package 123 may be used to focus the laser beam 120 into a toroidal cross-section, so that laser beam 120 substantially surrounds inner electrode 112. Instead of an ion shutter, laser beam 120 may be pulsed to produce groups of ions 122 (i.e., similar to ion bands 23, FIG. 4), which are then detected by detector 124.

Referring back now primarily to FIGS. 1 and 2, in one embodiment, inner electrode 12 may comprise an ejection electrode 34 that is generally aligned with longitudinal axis 32 of ion mobility spectrometer 10. As will be described in greater detail below, ejection electrode 34 is used in combination with various other elements of inner electrode 12 to assist in the selective release of ions 22 into the drift region 18. Ejection electrode 34 may comprise a generally cylindrically shaped, rod-like element having a proximal end 36 positioned adjacent the ion formation region 26.

Ejection electrode 34 may be fabricated from any of a wide range of electrically conductive materials (e.g., metals) suitable for the intended application, as would become apparent to persons having ordinary skill in the art after having become familiar with the teachings provided herein. By way of example, in one embodiment, ejection electrode 34 is fabricated from stainless steel.

Inner electrode 12 may also comprise a first control electrode 38 that is positioned adjacent ejection electrode 34 so that at least a portion of the first control electrode 38 surrounds at least a portion of ejection electrode 34. A plurality of insulating support members or "spiders" 40 may be used to hold ejection electrode 34 and first control electrode 38 in spaced-apart, generally concentric relation and to allow different electrostatic potentials to be placed on the ejection electrode 34 and first control electrode 38 in a manner that will be described in further detail below. Alternatively, other mounting arrangements are possible, as would become apparent to persons having ordinary skill in the art after having become familiar with the teachings provided herein. Consequently, the particular mounting arrangement utilized in one embodiment will not be described in further detail herein.

First control electrode 38 may be fabricated from any of a wide range of electrically conductive materials (e.g., metals) suitable for the particular application. By way of example, in one embodiment, first control electrode 38 is fabricated from stainless steel. The thickness of first control electrode 38 is not particularly critical, although it will generally be desirable to make it as thin as possible, consistent with the mechanical strength requirements of the particular application. By way of example, in one embodiment, first control electrode 38 may have a thickness of about 0.3 mm (about 0.012 inches).

First control electrode 38 may be provided with a grid section 42 that is substantially aligned with the drift space 18. In the embodiment shown and described herein, grid section 42 comprises a portion of ion shutter 30. That is, grid section 42 allows ions 22 from ion tunnel 28 to be released into the drift space 18 when the proper electrostatic charge is placed on grid section 42. Conversely, grid section 42 will not allow ions 22 to be released into the drift space 18 if the electrostatic charge on grid section 42 is configured so as to repel the ions 22.

Grid section 42 may comprise a separate wire mesh or screen-like member that is fastened to first control electrode 38 by any of a wide variety of methods (e.g., welding). Alternatively, grid section 42 could comprise an integral portion of first control electrode 38, being formed by any of a wide variety of processes (e.g., electro-forming) known in the art. The thickness of the material (e.g., wire screen) comprising grid section 42 should be made as thin as possible to reduce ion loss to the grid section 42 as the ions 22 pass through grid section 42. By way of example, in one embodiment, the wire screen comprising grid section 42 has a thickness of about 0.033 mm (about 0.0013 inches).

Inner electrode 12 may also comprise a second control electrode 44. Second control electrode is positioned adjacent the first control electrode 38 so that at least a portion of the second control electrode 44 surrounds at least a portion of the first control electrode 38. A pair of insulating support members 46 may be used to hold first and second control electrodes 38 and 44 in spaced-apart, generally concentric relation and to allow different electrostatic potentials to be placed on the first and second control electrodes 38 and 44. Alternatively, other mounting arrangements could be utilized, as would become apparent to persons having ordinary skill in the art after having become familiar with the teachings provided herein.

Second control electrode 44 may be fabricated from any of a wide range of electrically conductive materials (e.g., metals) suitable for the particular application. By way of example, in one embodiment, second control electrode 44 is fabricated from copper. The thickness of second control electrode 44 is not particularly critical, although it will generally be desirable to make it as thin as possible, consistent with the mechanical strength requirements of the particular application. By way of example, in one embodiment, second control electrode 44 may have a thickness of about 0.2 mm (about 0.008 inches).

Second control electrode 44 may be provided with a grid section 48 that is substantially aligned with drift space 18 and grid section 42 of first control electrode 38. In the embodiment shown and described herein, the second control electrode 44 and grid section 48 are maintained at a constant electrostatic potential that is "matched" to the electrostatic field 16. The constant, matched electrostatic potential on second control electrode 44 and grid section 48 prevents detector 24 from "seeing" changes in the electrostatic field 16, thereby substantially preventing unwanted oscillations (e.g., ringing) in the signal from the detector 24.

As was the case for grid section 42 of first control electrode 38, grid section 48 of second control electrode 44 may comprise a separate wire mesh or screen-like member that is fastened to second control electrode 44. Alternatively, grid section 48 could comprise an integral portion of second control electrode 44, being formed by any of a wide variety of processes (e.g., electro-forming) known in the art. The thickness of the material (e.g., wire screen) comprising grid section 48 should be made as thin as possible to reduce ion loss to the grid section 48 as they pass through grid section 48. By way of example, in one embodiment, the wire screen comprising grid section 48 has a thickness of about 0.033 mm (about 0.0013 inches).

Before proceeding with the description, it should be noted that persons having ordinary skill in the art will recognize that the various electrodes (e.g., 12, 14, 34, 38, and 44) could be fabricated from wire mesh or even from wire extending along longitudinal axis 34, provided that a logarithmic electric field 16 can be maintained in the drift space or region 18. In still yet another variation, some of the electrodes, or even portions of the electrodes could be made solid, while other electrodes, or portions of the electrodes could be fabricated from wire mesh or wire. However, because persons having ordinary skill in the art will readily recognize that other electrode constructions (e.g., solid, wire, or a mixture thereof) are possible, after having become familiar with the teachings provided herein, various possible electrode constructions will not be described in further detail herein.

Inner electrode 12 may also be provided with an ion source or ionizing element 20 suitable for ionizing the sample material (not shown) provided to the ion mobility spectrometer 10. In one embodiment, ion source or ionizing element 20 may comprise a ring-shaped member having a radioactive isotope, such as $^{63}Ni$, provided thereon. $^{63}Ni$ is a beta emitter and is thus capable of ionizing most sample materials expected to be used with the ion mobility spectrometer 10. Alternatively, other ionizing materials may be used, as would become apparent to persons having ordinary skill in the art after having become familiar with the teachings provided herein.

In one embodiment, ion source 20 may comprise an open (i.e., hollow) cylinder or ring-shaped member on which is deposited the nickel-63. In one embodiment, the ring-shaped member may comprise a nickel alloy (e.g., nickel 200). Alternatively, ion source 20 need not comprise a separate member. For example, in another embodiment, ion source 20 could instead comprise a portion of the first control electrode 38 itself. That is, a suitable ionizing material (e.g., $^{63}$Ni) could be provided (e.g., deposited) directly on an end portion 49 of first control electrode 38 itself. Still other arrangements are possible, as would become apparent to persons having ordinary skill in the art after having become familiar with the teachings provided herein. Consequently, the present invention should not be regarded as limited to any particular ionizing source 20.

In the embodiment shown and described herein, the sample material to be ionized may be introduced into the ion mobility spectrometer 10 by gas flow means 50 operably associated with the first control electrode 38. More specifically, gas flow means 50 may be used to provide a flow of a carrier gas, such as air, (illustrated by arrow 52) axially along the ion tunnel 28 defined by first control electrode 38. Carrier gas 52 may be used to carry the sample material (e.g., also in gaseous form or aerosol) to the ionizing source 20. Thereafter, ionizing source 20 ionizes the sample material in the ion formation region 26 of ion tunnel 28.

Gas flow means 50 may comprise any of a wide range of elements and systems for providing a flow of carrier gas 52, along with entrained sample material, to the ion mobility spectrometer 10. For example, in one embodiment, gas flow means 50 could comprise a pressurized gas inlet 54 operatively associated with the first control electrode 38 for introducing the carrier gas 52 (e.g, air) at a position generally upstream of ion source or ionizing element 20. Alternatively, gas flow means 50 could comprise a pump 56 operatively associated with the first control electrode 38 (i.e., ion tunnel 28) at a position downstream of the ion shutter 30. In yet another arrangement, a combination of a pressurized gas inlet 54 and a pump 56 may be utilized. Still other arrangements are possible, as would become apparent to persons having ordinary skill in the art after having become familiar with the teachings provided herein. Consequently, the present invention should not be regarded as limited to any particular type of gas flow means 50.

The velocity of the carrier gas 52 provided by gas flow means 50 may comprise any of a wide range of velocities depending on the particular configuration, operational parameters, and sample materials to be analyzed by the ion mobility spectrometer 10. Consequently, the present invention should not be regarded as limited to any particular velocity of carrier gas 52. However, by way of example, in one embodiment, a velocity of carrier gas 52 within ion tunnel 28 of about 1 meter/second (m/s) was found to provide good results and minimize losses of ions 22 due to diffusion and subsequent collision with ion tunnel 28 and ejection electrode 34.

As mentioned above, outer electrode 14 may, in one embodiment, comprise a generally hollow, cylindrically-shaped structure that substantially surrounds inner electrode 12 in the manner already described. Outer electrode 14 should be mounted so that it is electrically insulated from inner electrode 12, i.e., so that the two electrodes 12 and 14 can be maintained at different electrostatic potentials. Outer electrode 14 may comprise any of a wide variety of electrically conductive materials (e.g., metals) that would be suitable for the intended application. By way of example, in one embodiment, outer electrode 14 comprises stainless steel. The thickness of outer electrode 14 is not particularly critical and may comprise any of a wide range of thicknesses consistent with the mechanical strength requirements of the particular application. By way of example, in one embodiment, outer electrode 14 may have a thickness of about 6.5 mm (about 0.26 inches).

As will be described in further detail below, it is generally preferred that the electrostatic field 16 be substantially distortion-free in the drift region 18, as best seen in FIG. 3. To help achieve such a distortion-free field 16, ion mobility spectrometer 10 may be provided with a first end plate electrode 58 positioned at about a first end 60 of outer electrode 14 and a second end plate electrode 62 positioned at about a second end 64 of outer electrode 14. The first and second end plate electrodes 58 and 62 help to terminate the electrostatic field 16 in a way that minimizes distortion in a central region of the field, i.e., generally that region that coincides with drift region 18.

First end plate electrode 58 may comprise an outer section 66 and an inner section 68 that are electrically insulated from one another so that different electrostatic potentials may be placed on the outer and inner sections 66 and 68 of first end plate electrode 58. Similarly, second end plate electrode 62 may comprise an outer section 70 and an inner section 72 that are electrically insulated from one another so that different electrostatic potentials may be placed on the outer and inner sections 70 and 72 of second end plate electrode 62. As illustrated in FIG. 3, and as will be described in greater detail below, the first and second end plate electrodes 58 and 62 help to terminate the electrostatic field 16 between inner electrode 12 and outer electrode 14 so that a desirable, i.e., a substantially distortion-free, field 16 exists throughout the drift region 18.

A detector 24 may be provided adjacent outer electrode 14 and is generally aligned with drift region 18 so that ions 22 traversing drift region 18 will impinge on detector 24. Referring now primarily to FIG. 2(a), in one embodiment, detector 24 may comprise a laminated or layered structure having first and second electrically conductive layers 74 and 76 separated by an insulator 78. Second layer 76 may be adhered or affixed to outer electrode 14 by means of a suitable adhesive layer 80. As will be described in greater detail below, first layer or detector layer 74 receives ions 22 from drift space 18. Second layer 76 may be electrically biased to form the ground plane for the detector layer 74 that captures the ions. That is, second layer 76 may comprise a ground plane layer. In this way, any imperfections in adhering the laminated detector 24 to the outer electrode 14 will not affect the ground plane for detector layer 74, which could result in increased noise.

The first and second electrically conductive layers 74 and 76 comprising laminated detector 24 may be fabricated from any of a wide variety of electrically conductive materials (e.g., metals) suitable for the intended application. Insulator 78 may comprise any of a wide range of insulating materials suitable for use in the intended application and that would be suitable for use with the particular materials selected for the first and second electrically conductive layers 74 and 76. Consequently, the present invention should not be regarded as limited to any particular materials for laminated detector 24. However, by way of example, in one embodiment, detector 24 may be formed from a flexible, double-layer copper printed circuit board material adhered to the outer electrode 14 by a suitable adhesive, such as a metal leaf adhesive available from Mona Lisa Products, Houston Art, Inc., Houston, Tex. (US). In this particular example, then, the two electrically conductive layers 74 and 76 comprise metallic copper, whereas the insulator 78 comprises a polyimid film, such as Kapton®.

The physical dimensions (i.e., sizes) of the various components comprising the ion mobility spectrometer 10 may comprise any of a wide range of sizes depending on the particular application, the type of sample materials to be analyzed, certain performance requirements (e.g., the desired fractional resolving limit), and other factors, taken in conjunction with the teachings provided herein. Consequently, the present invention should not be regarded as limited to any particular physical dimensions or sizes for the various components. However, by way of example, in one embodiment, the overall length 82 of ion mobility spectrometer 10 may be about 17.8 cm (about 7 inches). Consequently, the overall lengths of the inner and outer electrodes 12 and 14 may be selected to be substantially identical to the overall length 82. If a multi-component inner electrode 12 is utilized, as illustrated in FIGS. 1 and 2, the overall lengths of the first and second control electrodes 38 and 44 also may be selected to be substantially identical to the overall length 82.

The inside diameter 84 of the outer electrode 14 may, in one embodiment, comprise about 17.8 cm (about 7 inches). The outside diameter 86 of inner electrode 12 should be made as small as practical to minimize the inside diameter 84 of outer electrode 14 that would be required to provide the ion mobility spectrometer 10 with a given width 96 of the drift space 18. In one example embodiment wherein the inside diameter 84 of outer electrode is about 17.8 cm (about 7 inches), the outside diameter 86 of inner electrode 12 (i.e., the second control electrode 44) is about 17.8 mm (about 0.7 inches). Accordingly, the width 96 of drift space 18 will be about 92 mm (about 3.65 inches). The outside diameter 88 of first control electrode 38 may be about 11.9 mm (about 0.47 inches). The outside diameter 90 of ejection electrode 34 may be about 6 mm (about 0.24 inches).

As previously mentioned, the proximal end 36 of ejection electrode 34 terminates at a position between ion source 20 and ion shutter 30. In one embodiment, the ion source 20 and the proximal end 36 of ejection electrode 34 are separated by a distance that exceeds the beta effective range of the ionizing material. This separation is provided for safety reasons and to prevent unwanted ionization within the region of the ion shutter 30. In one embodiment, the beta effective range (in air) of the $^{63}$Ni ionizing material is about 30 mm (about 1.18 inches). Consequently, the proximal end 36 of ejection electrode 34 may be positioned so that it is located about 50 mm (about 1.97 inches) from ionizing source 20.

The various electrodes 12, 14, 34, 38, 44, 68, and 72 comprising the ion mobility spectrometer 10 may be connected to a voltage source 92 capable of placing the desired voltage potentials on the various electrodes to achieve the operational states described herein. Voltage source 92 may comprise any of a wide range of systems and devices currently known in the art or that may be developed in the future that are, or would be, capable of providing the desired voltage potentials on the various electrodes in accordance with the teachings provided herein. However, because voltage sources suitable for placing voltage potentials on electrodes of ion mobility spectrometers are well-known in the art and could be readily provided by persons having ordinary skill in the art after having become familiar with the teachings provided herein, the particular voltage source 92 that may be utilized in conjunction with the ion mobility spectrometer 10 will not be described in further detail herein.

The detector 24 may be connected to a signal processing system 94 suitable for detecting ions 22 impinging detector 24. Signal processing system 94 may comprise any of a wide range of systems and devices currently known in the art or that may be developed in the future that are, or would be, capable of detecting signals from detector 24 and processing those signals so that meaningful information may be obtained. However, because signal processing systems suitable for use with detectors in ion mobility spectrometers are well-known in the art and could be readily provided by persons having ordinary skill in the art after having become familiar with the teachings provided herein, the particular signal processing system 94 that may be utilized in conjunction with the ion mobility spectrometer 10 will not be described in further detail herein.

In order to prepare the ion mobility spectrometer 10 for operation, the voltage source 92 may be operated to place various voltage potentials on the various electrodes to establish the electrostatic fields required to achieve certain operational states. For example, and with reference now primarily to FIGS. 3 and 4, a non-liner (e.g., logarithmic) electrostatic field 16 may be produced by grounding (e.g., placing a ground potential on) the outer electrode 14. The outer sections 66 and 70 of respective first and second end plate electrodes 58 and 62 may also be placed at the same potential (e.g., ground potential) as the outer electrode 14. As mentioned, this will help to ensure that the electric field 16 is substantially distortion-free in the drift region 18. Second control electrode 44 of inner electrode 12 may be placed at various potentials depending on whether ions are to be released or blocked by the ion shutter 30, as will be described in greater detail below. Generally speaking, in one embodiment, the second control electrode 44 will be biased at a potential of about 1,000 volts (relative to outer electrode 14) and will remain constant. The inner sections 68 and 72 of respective first and second end plate electrodes 58 and 62 may be placed at the same potential as second control electrode 44. So placing the inner sections 68 and 72 of respective first and second end plate electrodes 58 and 62 helps to ensure that the electric field 16 is substantially distortion-free in the drift region 18.

A schematic representation of the logarithmic electric field 16 resulting from the potential electrostatic gradients is illustrated in FIG. 3. The electrostatic field 16 represented in FIG. 3 was generated by a computer modeling program known as "SIMION 7.0" which is available from Scientific Instruments Services, Inc., 1027 Old York Road, Ringoes, N.J. 08551 (US). The computer modeling is based on the ion mobility spectrometer 10 having the electrode configurations and dimensions shown and described herein. In addition, the electric fields and ion movements depicted in FIGS. 4-8 were also derived from the SIMION 7.0 computer program in conjunction with the Statistical Diffusion Simulation (SDS) user program package, which is available as supplementary material associated with the following journal article: Appelhans, A. D.; Dahl, D. A., "SIMION Ion Optics Simulations at Atmospheric Pressure," *International Journal of Mass Spectrometry* 2005, 244, 1-14, which is incorporated herein by reference for all that it discloses.

Referring now primarily to FIG. 3, the electrostatic field 16 created between the inner and outer electrodes 12 and 14 is logarithmic. The field 16 is also substantially distortion-free in the region of the drift space 18 due to the electrostatic charges placed on the various sections 66, 68, 70, and 72 of the end plate electrodes 58 and 62. Also illustrated in FIG. 3 are the paths followed by ions 22 exiting ion shutter 30 (only the ion paths on the upper portion of inner electrode 12 are depicted in FIG. 3).

Figure 6:
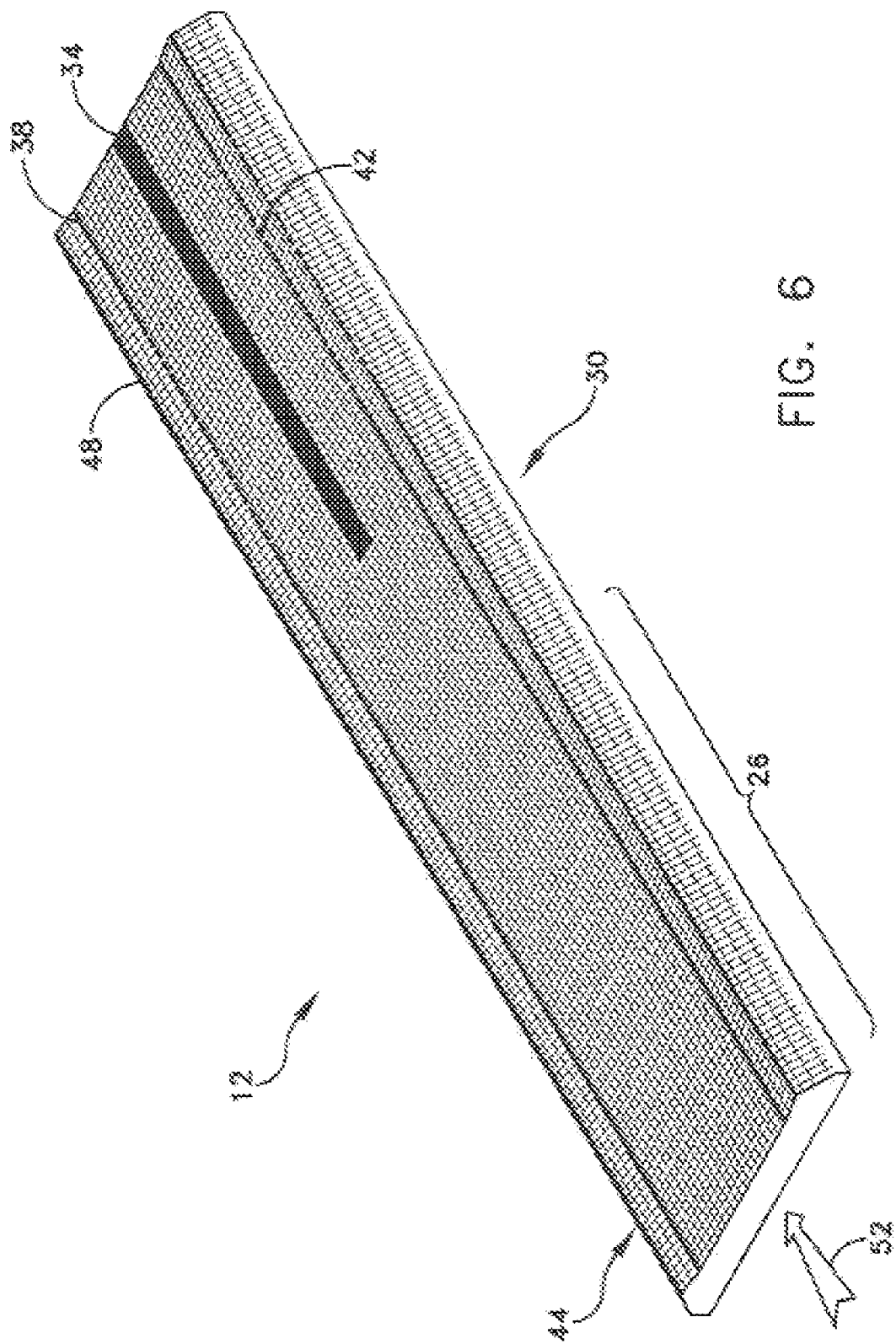
FIG. 6 is a potential energy surface view of an ion shutter assembly in ion pass through mode.

The various electrodes 34, 38, and 44 that may comprise inner electrode 12 may be operated to periodically release ions 22 into the drift region 18 defined between inner and outer electrodes 12 and 14. That is, various electrostatic potentials may be placed on electrodes 34, 38, and 44 to cause them to collectively operate as ion shutter 30. Referring now to FIG. 6, ions 22 formed in the ionization region 26 by the radioactivity (e.g., beta radiation) emitted by ionization source 20 (FIG. 1), are caused to flow down the ion tunnel 28 by the flow of carrier gas 52 established within first control electrode 38. However, the ions 22 cannot escape via the grid sections 42 and 48 due to the electrical potentials placed on them by voltage source 92. More specifically, in the embodiment illustrated in FIG. 6, the potentials on ejection electrode 34 and first control electrode 38 (including grid section 42) are set by the voltage source 92 so that they are substantially identical (e.g., about 990 volts). Second control electrode 44 and grid section 48 are placed at a slightly higher potential (e.g., about 1000 volts) by voltage source 92. The resulting 10 volt potential difference between grid section 42 and grid section 48 will prevent ions from being released into the drift region 18. Instead, ions 22 will continue traversing ion tunnel 28, whereupon they may be ultimately discharged.

Figure 7:
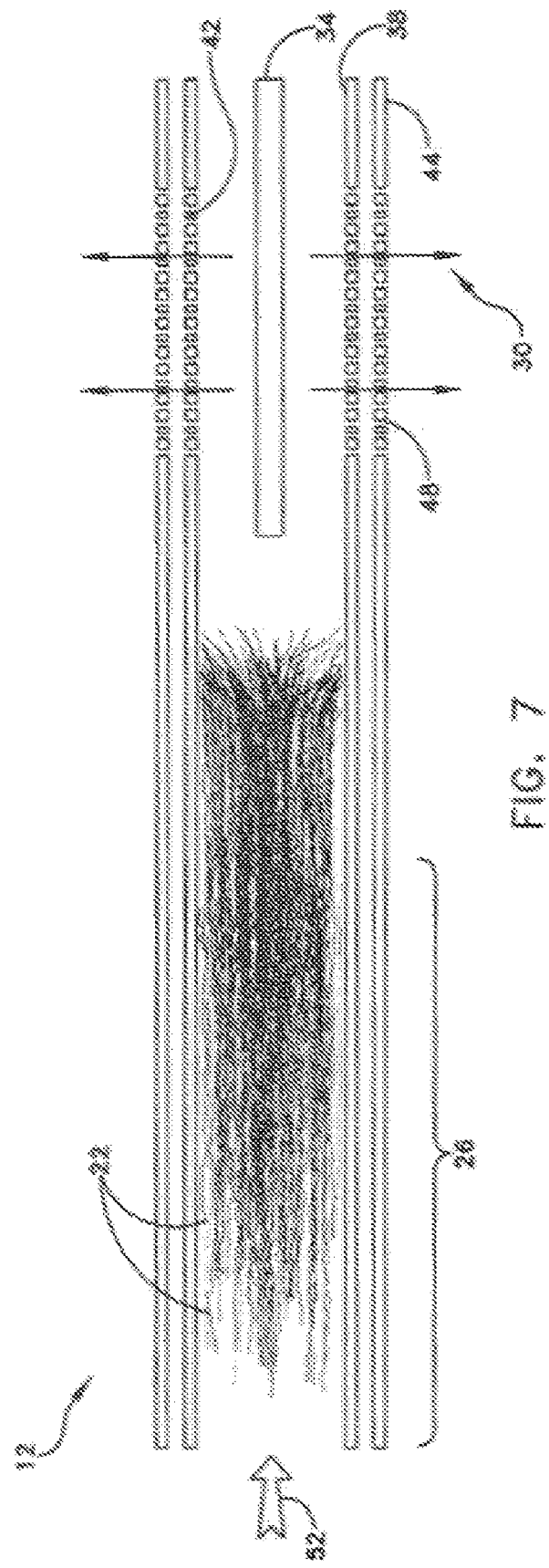
FIG. 7 is a side view simulation of the ion shutter assembly in ion blocking/release mode.

Ions 22 contained within ion tunnel 26 may be released to the drift space 18 by removing the blocking potential difference between the two grid sections 42 and 48 of respective first and second control electrodes 38 and 44, as best seen in FIG. 7. At the same time, ejection electrode 34 may be biased to block ions from the ionization region 26 during the ion release process, so that they do not interfere with the analysis process. When the ion shutter 30 is in this block/release mode, voltage source 92 places voltage potentials on grid section 42 and ejection electrode 34 that match the logarithmic voltage gradient between the outer grid section 48 and the detector 24 (which is at the same potential as outer electrode 14). For example, if the detector 24 is at 0 volts (i.e., ground potential), and the outer grid section 48 is at 1,000 volts, then the inner grid section 42 (and first control electrode 38) should be set at about 1,119 volts, and the ejection electrode 34 at about 1,956 volts. In this regard it should be noted that once a voltage on electrode 34, 38, or 44 is chosen, then the voltages on the other two electrodes are determined by the choice of radius of the inner electrode 12 and the outer electrode 14 to maintain a matching logarithmic voltage gradient. Schematic illustrations of electrostatic field potentials and ion flow associated with this ion blocking mode are illustrated in FIGS. 7 and 8.

Ion mobility spectrometer 10 may be operated as follows to detect ions 22. Consider, for example, an application wherein the sample material comprises gaseous or vapor-state material from a sampling region (not shown) operatively associated with ion mobility spectrometer 10. The sample material is conducted to the ionization source 20 by gas flow means 50. That is, the gaseous or vapor-state sample material will be entrained in the flow of carrier gas 52, as best seen in FIG. 1. When the carrier gas 52 (along with the entrained sample material) approach the ionization source 20, beta radiation from the ionization source 20 (e.g., $^{63}$Ni) will begin to ionize the sample material, resulting in the formation of ions 22 within ion formation region 26. As mentioned above, the beta-effective ionization range (in air) for nickel-63 is about 30 mm. Therefore, the ion formation region 26 may be coextensive with this length.

If the various electrodes (e.g., 34, 38, and 44) comprising ion shutter 30 are electrically biased so that ion shutter 30 is in ion pass through mode (e.g., as illustrated in FIG. 6), ions 22 produced by ionization source 20 will be confined within ion tunnel 28. That is, ions 22 will not be released into the drift region 18. Instead, ions 22 will be conducted along the length of ion tunnel 28, being ultimately discharged by ion mobility spectrometer 10.

Figure 8:
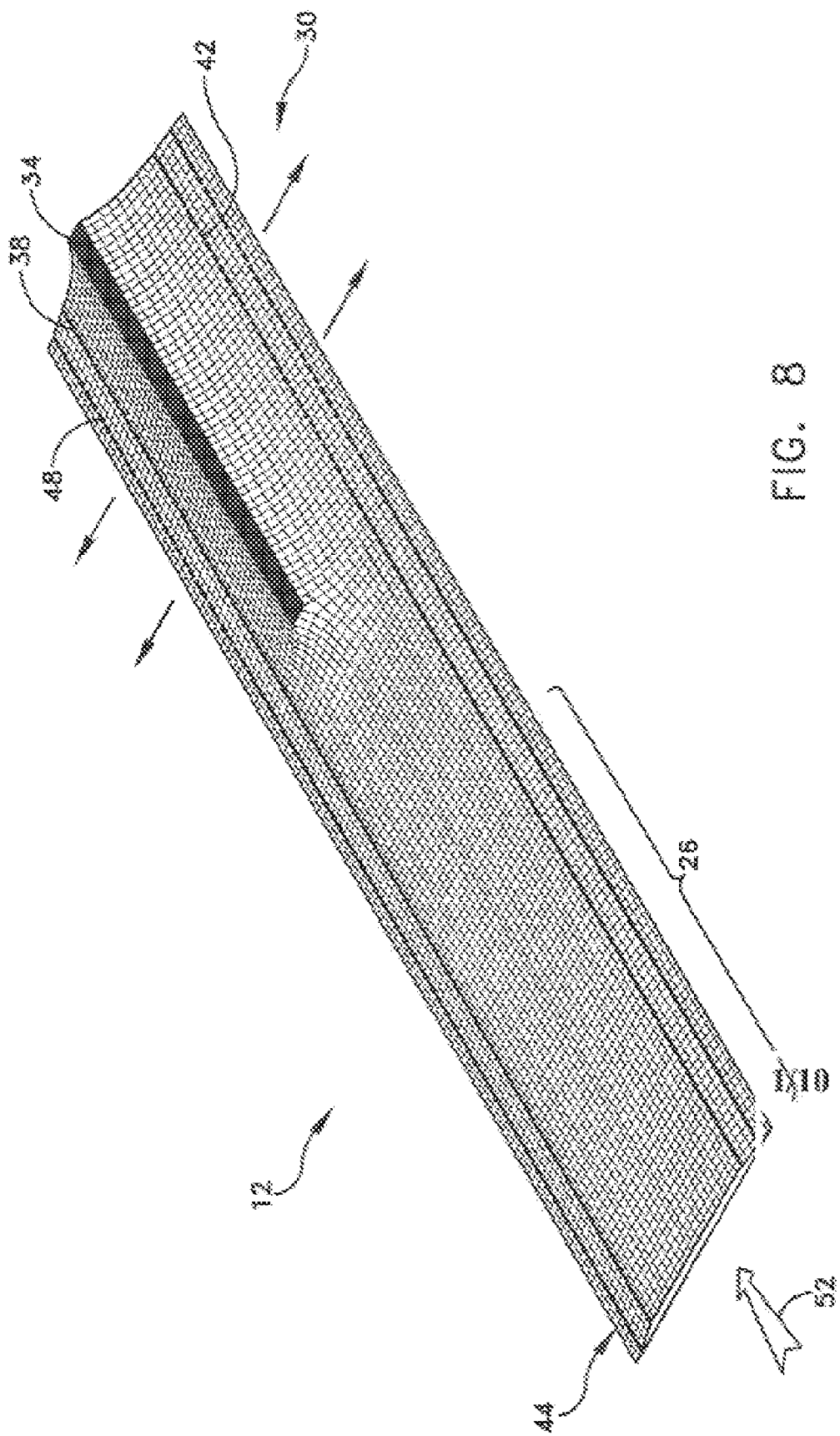
FIG. 8 is a potential energy surface view of the ion shutter assembly in ion blocking/release mode.

Once it is desired for ions 22 to be released into drift space 18, voltage source 92 may be operated to change the electrostatic potentials on electrodes 34, 38, and 44 in the manner already described so that ion shutter 30 is placed in the blocking/release mode, as illustrated in FIGS. 7 and 8. When operated in the blocking/release mode, the electrostatic potential placed on the first and second control electrodes 38 and 44, and more specifically respective grid sections 42 and 48, will allow ions 22 adjacent the grid sections 42 and 48 to be released into drift space 18. Meanwhile, the electrostatic potential placed on ejection electrode 34 creates a logarithmic voltage field that matches the logarithmic field 16 in drift region 18. Moreover, the potential serves to block ions 22 from ion source 20 from entering the ejection region, as best seen in FIG. 7. After the ion shutter 30 has been operated in the blocking/release mode for the desired period of time, the voltage source 92 may be operated to return the ion shutter 30 to the ion pass through mode, thereby preventing the further release of ions 22 into drift space 18.

Referring back now to FIGS. 3-5, ions 22 released by ion shutter 30 into drift space 18 will traverse drift space 18 in a generally radial direction before being detected by detector 24. See FIG. 3. As the ions 22 traverse drift space 18, the logarithmic electric field 16 will cause the ions 22 to be drawn to the outer electrode 14, with the radial movement of the ions 22 being inversely proportion to radius in viscous flow within the logarithmic electrostatic field 16. This motion will cause a band 23 of identical ions 22 to pack and become thinner as the band 23 moves outward, as best seen in FIGS. 4 and 5. The ion density also decreases as the bands 23 of ions 22 travel generally radially outwardly toward detector 24, thereby reducing ion spread due to charge-repulsion effects. Consequently, the ion mobility spectrometer 10 according to the teachings of the present invention can realize substantial increases in resolution (i.e., the fractional resolving limit), compared with currently-available ion mobility spectrometers having linear electrostatic fields with equivalent charge densities and ion drift times.

The fractional resolving limit of an ion mobility spectrometer according to the present invention is a function of the square of the radius of the ion mobility spectrometer 10, whereas the fractional resolving limit of a conventional drifttube IMS having a linear electrostatic field is a linear function of the drift length. Therefore, if two groups of ions 22 that vary in mobility by 1% have initial packet widths of about 1 cm, then in an ideal case, a linear IMS would require a drift length of about 100 cm to just separate or resolve the two ion packets, whereas the radius of the IMS 10 of the present invention would only need to be about 10 cm for the same initial ion packet width. Of course, both IMS systems would have to be slightly larger due to several factors (e.g., diffusion effects). Therefore, the squared relation of the fractional resolving limit of an ion mobility spectrometer according to the teachings provided herein will allow for thicker initial ion packets (for the same resolution) compared to a conventional IMS having a linear electrostatic field in the drift region. Alternatively, the resolution will be increased for ion packets of the same initial thickness.

The fractional resolving limit of the ion mobility spectrometer 10 is best understood by reference to FIGS. 4 and 5. In FIGS. 4 and 5, ions 22 having a slightly larger mobility are designated by number 25 and are depicted as solid square features, whereas ions 22 having a lower mobility are designated by the number 27 and are depicted by open square features. Shortly after released into the drift space (i.e., near the center of the spectrometer 10), the high and low mobility ions 25 and 27 are intermixed and not well-separated. However, as they drift outwardly toward detector 24, they are gradually separated. In the embodiment illustrated in FIGS. 4 and 5, the high and low mobility ions 25 and 27 are just resolved at detector 24.

With regard to space-charge tolerance, or sensitivity to charge-repulsion effects, computer modeling of the ion mobility spectrometer 10 of the present invention indicates that the present invention provides for an order-of-magnitude increase or more in space-charge tolerance. This tolerance increase is due to the gradual dispersion (i.e., reduction in ion density) as the ion bands 23 expand radially outwardly toward detector 24. In addition, the boundary-less expansion of ions 22 means ions 22 are not lost to the walls (e.g., drift tube walls) as they drift toward the detector, providing for significant increases in sensitivity.

Figure 10:
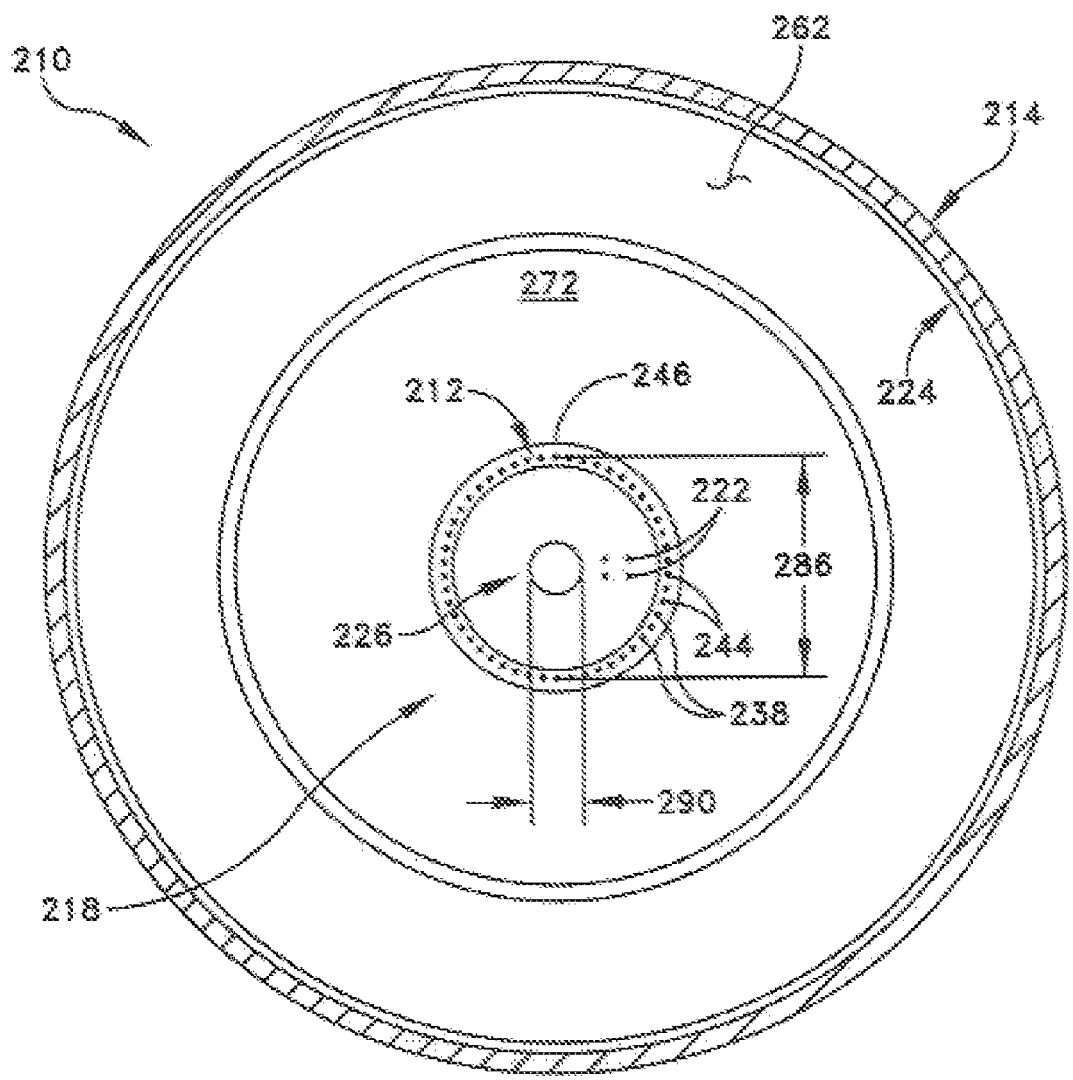
FIG. 10 is a cross-sectional end view in elevation of another embodiment of an ion mobility spectrometer having an alternating rod-like control electrode configuration.

Another embodiment 210 of an ion mobility spectrometer according to the teachings of the present invention is illustrated in FIG. 10. Embodiment 210 is similar to embodiment 10 already described, except that instead of an inner electrode (e.g., inner electrode 12) comprising generally concentric first and second control electrodes (e.g., first and second control electrodes 38 and 44), embodiment 210 includes an inner electrode 212 that comprises a plurality of wire-like or rod-like electrodes 238 and 244. More specifically, inner electrode 212 of embodiment 210 comprises an alternating arrangement of two sets 238 and 244 of wire-like or rod-like electrodes arranged so that they are generally concentric with ejection electrode 234. Embodiment 210 may also comprise an outer electrode 214 having a detector 224 positioned thereon in a manner identical or similar to that of first embodiment 10.

Each of the wire-like electrodes 238 and 244 comprising inner electrode 212 may be supported by a suitable insulating member 246 provided in inner section 272 of second end plate electrode 262. Of course, the wire-like electrodes 238 and 244 may be supported by a similar insulating member provided on the first end plate electrode (not shown) of embodiment 210. Alternatively, the wire-like electrodes 238 and 244 could be supported on a generally cylindrically shaped, tube like structure (not shown) with insulators (also not shown) provided as appropriate to support the expected voltage potentials. If such a support tube is used, it should be provided with a suitable opening or openings therein in the area of the drift space 218 to allow ions 222 to be released from ion tunnel 226 into the drift space 218 when the appropriate voltage potentials are placed on the wire-like electrodes 238 and 244 in a manner that will be described in greater detail below. Regardless of the particular arrangement utilized to support the wire-like electrodes 238 and 244, the insulators should be sized and/or positioned so as to minimize distortions in the electric fields in drift space 218 and ion tunnel 226.

The various wire-like electrodes 238 and 244 may be arranged around the ejection electrode 234 at any of a wide range of distances or spacings. By way of example, in one embodiment wherein ejection electrode 234 comprises a generally cylindrically shaped member having an outside diameter 290 of about 12.7 mm (about 0.5 inches), the various electrodes 238 and 244 are arranged around the ejection electrode 234 at a spacing or "inside diameter" 286 of about 50.8 mm (about 2 inches). A sufficient number of electrodes 238 and 244 is provided so that the radial spacing between any two adjacent electrodes (e.g., 238 and 244) is about 5.

The wire-like electrodes 238, 244 should be made as thin as possible to reduce ion losses to the electrodes 238 and 244 as the ions 222 are released from ion tunnel 226 into the drift space 218. By way of example, in one embodiment, each of the wire-like electrodes 238 and 244 has an outside diameter of about 0.76 mm (about 0.030 inches). Rod-like electrodes 238 and 244 may be fabricated from any of a wide range of electrically conductive materials (e.g., metals and metal alloys) that would be suitable for the intended application. By way of example, in one embodiment, each of the wire-like electrodes 238 and 244 is fabricated from a stainless-steel alloy. In one embodiment, each of the wire-like electrodes 238 and 244 comprises a substantially solid (e.g., rod-like element). Alternatively, each of the electrodes 238 and 244 may comprise a substantially hollow (e.g., a tube-like element), as would become apparent to persons having ordinary skill in the art after having become familiar with the teachings provided herein.

As mentioned, the various electrodes 238 and 244 comprising inner electrode 212 are arranged in an alternating manner. That is, alternating ones (e.g., 238) of electrodes are electrically connected together so that they can support a different electric potential than is placed on the other alternating ones (e.g., 244) of wire-like electrodes. The two groups of electrodes 238 and 244 may be electrically connected to a suitable voltage source (e.g., voltage source 92, FIG. 1) in the manner already described for the other embodiments.

During operation, the voltage source (e.g., voltage source 92, FIG. 1) may be operated to place various electrostatic potentials on the various electrodes (e.g., inner electrode 212, outer electrode 214, and ejection electrode 234) in a manner similar to that already described for the other embodiments. For example, in one embodiment, the electrodes may be operated in an ion blocking mode when the voltage source places a voltage potential of about 1010 volts on the wire-like electrodes 238, about 990 volts on the alternating pairs of wire-like electrodes 244, and about 1000 volts on the ejection electrode 234. Ions 222 contained within ion tunnel 226 may be released to the drift space 218 by increasing the voltage on the ejection electrode 234 to about 2000 volts, while placing a voltage of about 1000 volts on both sets of wire-like electrodes 238 and 244. The fractional resolving limit of embodiment 210 is about 6% compared to about 5% for embodiment 10.

Having herein set forth preferred embodiments of the present invention, it is anticipated that suitable modifications can be made thereto which will nonetheless remain within the scope of the invention. The invention shall therefore only be construed in accordance with the following claims:

The invention claimed is:

1. An ion mobility spectrometer, comprising:
   an inner electrode;
   an outer electrode, at least a portion of said outer electrode surrounding at least a portion of said inner electrode and defining a drift space between at least a portion of said inner electrode and at least a portion of said outer electrode, said inner and outer electrodes being electrically insulated from one another so that a non-linear electric field is created in the drift space when an electric potential is placed on said inner and outer electrodes;
   an ion source operatively associated with said ion mobility spectrometer, said ion source releasing ions to the drift space; and a detector operatively associated with at least a portion of said outer electrode, said detector detecting ions from the drift space.

2. The ion mobility spectrometer of claim 1, wherein said outer electrode comprises a generally cylindrically-shaped structure.

3. The ion mobility spectrometer of claim 2, wherein said inner electrode is generally aligned with a longitudinal axis of said generally cylindrically-shaped outer electrode.

4. The ion mobility spectrometer of claim 3, wherein said inner electrode further comprises:
an ejection electrode;
a first set of wire-like electrodes, at least a portion of which surround at least a portion of said ejection electrode; and
a second set of wire-like electrodes, at least a portion of which surround at least a portion of said ejection electrode.

5. The ion mobility spectrometer of claim 4, wherein said first set of wire-like electrodes and said second set of wire-like electrodes are arranged in an alternating manner around at least a portion of said ejection electrode.

6. The ion mobility spectrometer of claim 5, wherein said first and second sets of wire-like electrodes are spaced substantially equal distances from said ejection electrode.

7. The ion mobility spectrometer of claim 5, wherein a radial spacing between a wire-like electrode comprising said first set and a wire-like electrode comprising said second set is about 5°.

8. The ion mobility spectrometer of claim 7, wherein said inner electrode further comprises:
an ejection electrode;
a first control electrode, at least a portion of said first control electrode surrounding at least a portion of said ejection electrode; and
a second control electrode, at least a portion of said second control electrode surrounding at least a portion of said first control electrode, said ejection electrode, said first control electrode, and said second control electrode being electrically insulated from one another.

9. The ion mobility spectrometer of claim 8, wherein said first control electrode comprises a grid section therein and wherein said second control electrode comprises a grid section therein, the grid sections of said first and second control electrodes being generally aligned with one another and with the drift space.

10. The ion mobility spectrometer of claim 9, wherein said ion source is positioned within said first control electrode and located a spaced-distance from an end of said ejection electrode so that ions may be released into the drift space through the grid sections of said first and second control electrodes.

11. The ion mobility spectrometer of claim 10 further comprising gas flow means operatively associated with said first control electrode for providing for a flow of gas axially along said first control electrode, said flow of gas carrying ions from an ionization region to said grid section.

12. The ion mobility spectrometer of claim 11, wherein said gas flow means comprises a pressurized gas inlet operatively associated with said first control electrode at a position upstream of said ion source.

13. The ion mobility spectrometer of claim 11, wherein said gas flow means comprises a pump operatively associated with said first control electrode at a position downstream of said grid section.

14. The ion mobility spectrometer of claim 10, wherein said ion source comprises $^{63}$Ni.

15. The ion mobility spectrometer of claim 1, wherein said inner and outer electrodes comprise first and second ends, said ion mobility spectrometer further comprising a first end plate electrode positioned at about the first ends of said inner and outer electrodes and a second end plate electrode positioned at about the second ends of said inner and outer electrodes.

16. The ion mobility spectrometer of claim 15, wherein said first end plate electrode comprises an outer section and an inner section that are electrically insulated from one another, and wherein said second end plate electrode comprises an outer section and an inner section that are electrically insulated from one another.

17. The ion mobility spectrometer of claim 1, wherein said ion source comprises a laser, a laser beam produced by said laser being directed adjacent said inner electrode and in said drift space, the laser beam ionizing a sample material contained within said ion mobility spectrometer.

18. The ion mobility spectrometer of claim 1, wherein said detector is affixed to an inner surface of said outer electrode at a location that is generally aligned with the drift space.

19. An ion mobility spectrometer, comprising:
an inner electrode, said inner electrode comprising:
a generally elongate, cylindrically-shaped ejection electrode;
a first generally elongate, cylindrically-shaped control electrode surrounding at least a portion of said ejection electrode and electrically insulated therefrom, said first control electrode comprising a grid section located between first and second ends of said first control electrode;
a second generally elongate, cylindrically-shaped control electrode surrounding at least a portion of said first control electrode and electrically insulated therefrom, said second control electrode comprising a grid section located between first and second ends of said second control electrode and generally aligned with the grid section of said first control electrode;
a generally elongate, cylindrically shaped outer electrode surrounding at least a portion of said second control electrode and electrically insulated therefrom so that a drift space is defined generally in a region between said outer electrode and said second control electrode and generally aligned with the grid sections of said first and second control electrodes, a cylindrical gradient electric field being created in the drift space when an electric potential is placed on said inner and outer electrodes;
an ion source operatively associated with said ion mobility spectrometer, said ion source releasing ions into the drift space; and
a detector operatively associated with at least a portion of said outer electrode, said detector detecting ions from the drift space.

20. An ion mobility spectrometer, comprising:
an inner electrode;
an outer electrode, at least a portion of said outer electrode surrounding at least a portion of said inner electrode and defining a drift space between at least a portion of said inner electrode and at least a portion of said outer electrode;
a voltage source operatively connected to said inner electrode and to said outer electrode, said voltage source placing an electric potential on said inner and outer electrodes, said electric potential creating a non-linear electric field in the drift space;
an ion source operatively associated with said ion mobility spectrometer, said ion source releasing ions to the drift space; and a detector mounted to at least a portion of said outer electrode, said detector detecting ions from the drift space.

21. A method for performing ion mobility spectrometry, comprising:

releasing ions in a logarithmic electric field;

allowing the ions to drift within the logarithmic electric field; and detecting the ions at a detector.

22. The method of claim 21, wherein releasing ions into a logarithmic electric field comprises periodically releasing ions into the logarithmic electric field.

23. The method of claim 21, further comprising using a pulsed laser beam to create ions before releasing ions in the logarithmic electric field.

* * * * *